(12) United States Patent
Yamada

(10) Patent No.: US 9,520,434 B2
(45) Date of Patent: Dec. 13, 2016

(54) IMAGE PICKUP MODULE

(71) Applicant: OLYMPUS CORPORATION, Tokyo (JP)

(72) Inventor: Masashi Yamada, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 12 days.

(21) Appl. No.: 14/504,644

(22) Filed: Oct. 2, 2014

(65) Prior Publication Data

US 2015/0014805 A1    Jan. 15, 2015

Related U.S. Application Data

(63) Continuation of application No. PCT/JP2013/052544, filed on Feb. 5, 2013.

(30) Foreign Application Priority Data

Apr. 5, 2012 (JP) .................................. 2012-086723

(51) Int. Cl.
| | | |
|---|---|---|
| *H01L 27/146* | (2006.01) | |
| *H01L 31/0224* | (2006.01) | |
| *H04N 5/225* | (2006.01) | |
| *G03B 17/02* | (2006.01) | |
| *A61B 1/00* | (2006.01) | |
| *A61B 1/05* | (2006.01) | |
| *G03B 17/17* | (2006.01) | |

(52) U.S. Cl.
CPC ... *H01L 27/14636* (2013.01); *H01L 27/14618* (2013.01); *H01L 27/14625* (2013.01); *H01L 31/0224* (2013.01); *H04N 5/2254* (2013.01); *A61B 1/0011* (2013.01); *A61B 1/05* (2013.01); *G03B 17/02* (2013.01); *G03B 17/17* (2013.01); *H01L 2924/0002* (2013.01); *H04N 2005/2255* (2013.01)

(58) Field of Classification Search
CPC ............. H01L 21/4821; H01L 2021/60; H01L 23/495; H01L 23/498; H01L 23/52; H01L 23/522
See application file for complete search history.

(56) References Cited

U.S. PATENT DOCUMENTS

| | | | |
|---|---|---|---|
| 6,909,173 B2* | 6/2005 | Hamamoto | ......... H01L 23/4985 257/690 |
| 2001/0050721 A1* | 12/2001 | Miyake | ......................... 348/374 |
| 2011/0224487 A1* | 9/2011 | Ogawa | ................. A61B 1/0011 600/109 |

FOREIGN PATENT DOCUMENTS

| | | |
|---|---|---|
| JP | 07-142690 A | 6/1995 |
| JP | 08-131400 A | 5/1996 |
| JP | 09-146011 A | 6/1997 |

(Continued)

OTHER PUBLICATIONS

International Search Report dated Mar. 12, 2013 issued in PCT/JP2013/052544.

*Primary Examiner* — Jerome Jackson, Jr.
*Assistant Examiner* — David Spalla
(74) *Attorney, Agent, or Firm* — Scully, Scott, Murphy & Presser, P.C.

(57) ABSTRACT

An image pickup module includes: an image pickup chip including a main surface on which a light-receiving portion of an image pickup device and a plurality of electrodes connected to the light-receiving portion are formed; and a wiring board including flying leads bonded to the respective plurality of electrodes.

7 Claims, 4 Drawing Sheets

(56) References Cited

FOREIGN PATENT DOCUMENTS

| | | |
|---|---|---|
| JP | 11-354766 A | 12/1999 |
| JP | 2001-017389 A | 1/2001 |
| JP | 2006-055531 A | 3/2006 |
| JP | 2010-268077 A | 11/2010 |
| JP | 2011-192808 A | 9/2011 |
| JP | 2011-249870 A | 12/2011 |
| JP | 2012-055489 A | 3/2012 |

* cited by examiner

IMAGE PICKUP MODULE

CROSS REFERENCE TO RELATED APPLICATION

This application is a continuation application of PCT/JP2013/052544 filed on Feb. 5, 2013 and claims benefit of Japanese Application No. 2012-086723 filed in Japan on Apr. 5, 2012, the entire contents of which are incorporated herein by this reference.

BACKGROUND OF THE INVENTION

1. Field of the Invention

The present invention relates to an image pickup module including: an image pickup chip on which a light-receiving portion of a solid-state image pickup device is formed; and a wiring board.

2. Description of the Related Art

Japanese Patent Application Laid-Open Publication No. 2011-1192808 discloses an image pickup module 110 in which a prism 150 is disposed at a light-receiving portion 121 of a solid-state image pickup device, through a transparent member 140. In addition, a bump 123, which is connected with the light-receiving portion 121 through an internal wiring 124 and a connecting electrode 122, is bonded to a bonding electrode 131 of a wiring board 130, thereby reducing the size of the image pickup module.

The end surface 130L of the wiring board 130 and the end surface 120L of the image pickup chip 120 overlap each other. Therefore, at the time of bonding, the positions of the bump 123 and the bonding electrode 131 which are located on the rear surface of the wiring board 130 cannot be directly and visually checked.

Note that the above-described publication recites that a wiring board having a flying lead is positively excluded.

SUMMARY OF THE INVENTION

An image pickup module according to an embodiment of the present invention includes: an image pickup chip including a main surface on which a light-receiving portion of an image pickup device and a plurality of electrodes connected to the light-receiving portion are formed; and a wiring board including flying leads bonded to the respective plurality of electrodes.

DETAILED DESCRIPTION OF THE PREFERRED EMBODIMENTS

First Embodiment

Figure 1:
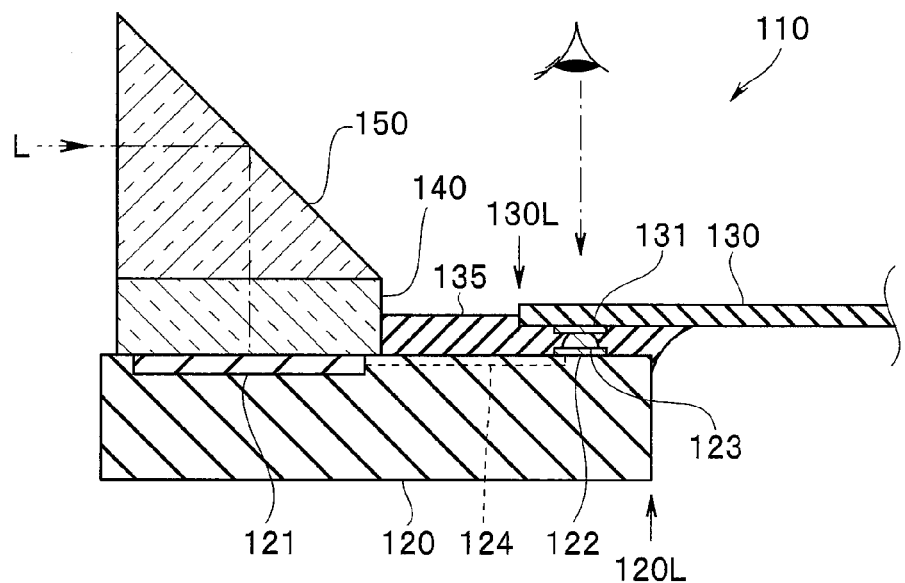
FIG. 1 is a cross-sectional view showing a configuration of a conventional image pickup module.
Figure 2:
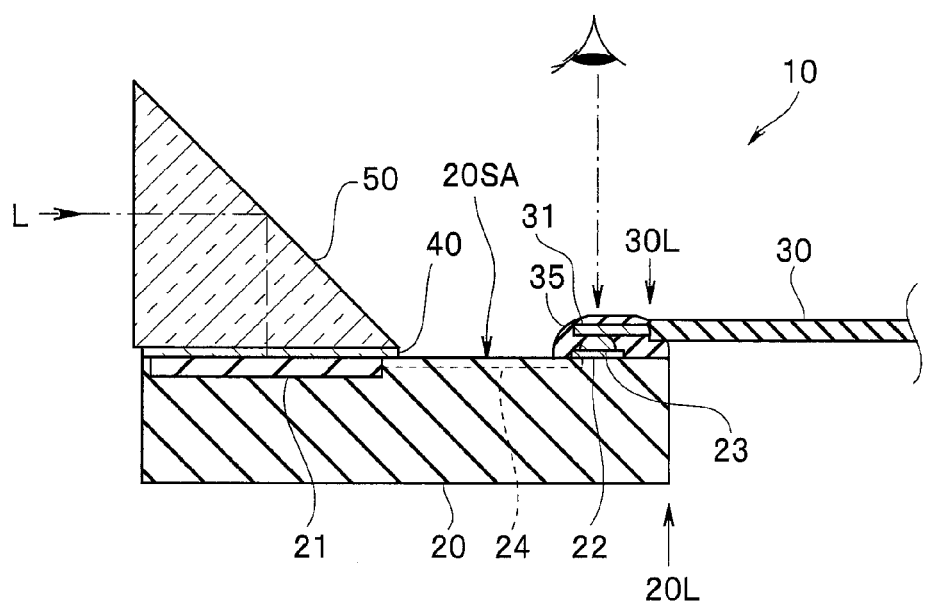
FIG. 2 is a cross-sectional view showing a configuration of an image pickup module according to a first embodiment.
Figure 3:
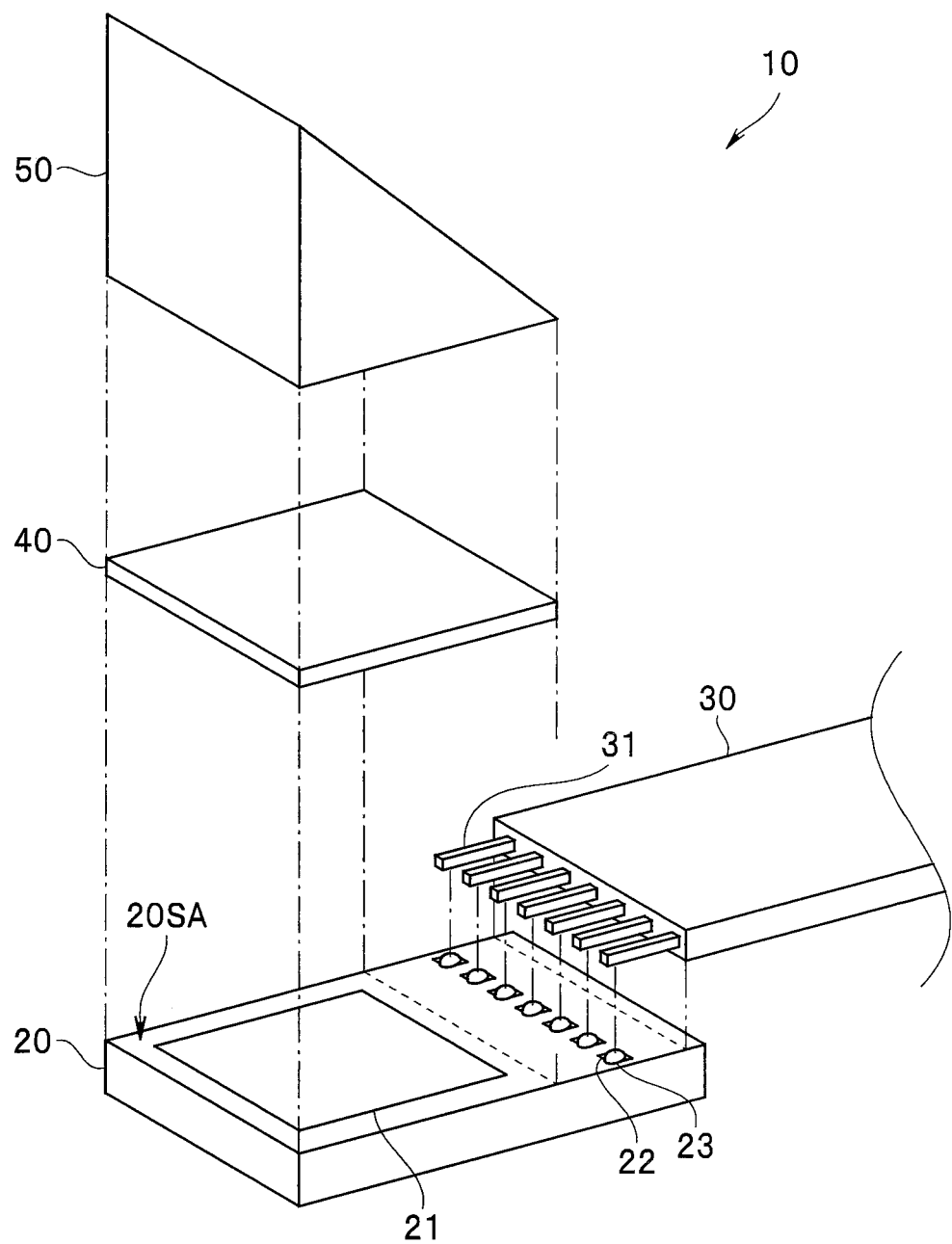
FIG. 3 is a perspective view showing disassembly and assembly of the image pickup module according to the first embodiment.

As shown in FIGS. 2 and 3, an image pickup module 10 according to the present embodiment includes an image pickup chip 20 to which a wiring board 30 and a prism 50 are bonded. On a main surface 20SA of the image pickup 20, a light-receiving portion 21 of a solid-state image pickup device and a plurality of electrodes 22 connected to the light-receiving portion 21 through an internal wiring 24 are formed. The plurality of electrodes 22 are bonded respectively to flying leads 31 of the wiring board 30 through bumps 23. Note that, in the image pickup module 10, an end surface 20L on a rear end side of the image pickup 20 and an end surface 30L on a distal end side of the wiring board 30 overlap each other.

Each of the flying leads 31 is made of a conducting body protruded from the end surface 30L of the wiring board 30 by a predetermined amount, and formed by removing an insulation layer covering the internal wiring of the wiring board 30. That is, the end surface 30L is the end surface of the insulation layer of the wiring board 30. The flying leads 31 are sealed by a sealing resin 35 together with the end surface 30L of the wiring board 30.

The prism 50 is an optical component that changes a direction of incident light such that incident light L entered from the direction parallel to the main surface 20SA of the image pickup chip 20 is incident on the light-receiving portion 21. The prism 50 is bonded to the upper surface of the light-receiving portion 21 through a transparent adhesion layer 40.

Next, a manufacturing method of the image pickup module 10 will be described.

An image pickup substrate is manufactured by a plurality of light-receiving portions 21 and a plurality of electrodes 22 connected to the respective light-receiving portions 21 being formed on the main surface 20SA of a silicon wafer by a known semiconductor process. Then, the image pickup substrate is cut, and thereby a plurality of image pickup chips 20 are created.

A material for the adhesion layer 40 that bonds the prism 50 to the light-receiving portions 21 of the image pickup chip is selected from a transparent resin, for example, an UV curable resin or a thermo-curing resin such as a silicone resin, an epoxy resin, an acrylic resin, or the like.

Electric bonding between the electrodes 22 of the image pickup chip 20 and the flying leads 31 of the wiring board 30 is performed by applying energy to the distal end portions of the flying leads 31 directly from upside of the distal end portions of the flying leads while performing positioning between the electrodes and the flying leads.

The image pickup module 10 is extremely small so as to be able to be disposed at the distal end portion of the endoscope having a thin diameter. The prism 50 has an incident surface of 1.0 mm square, and the wiring board 30 has a length of 1.5 mm in the major axis direction, a length of 1.0 mm in the minor axis direction, and the thickness of 0.2 mm, for example. In addition, the electrodes 22 each having 50 μm square are arranged in a line so as to have a space of 50 μm between the electrodes, and each of the flying leads 31 has a width of 50 μm, a thickness of 20 μm, and a length of 200 μm, for example.

Therefore, accurate positioning is essential. In the image pickup module 10, the width of each of the flying leads 31 is substantially equal to or smaller than the size (width) of each of the electrodes 22. Accordingly, the bonding positions on the main surface 20SA can be confirmed while visually checking the bonding positions from upside of the main surface. That is, the bonding positions can be adjusted while viewing the video image obtained by a digital microscope, for example. Then, energy is applied in the state where the positions of the electrodes 22 are aligned with the positions of the flying leads 31, which enables the electrodes and the flying leads to be surely bonded at predetermined positions.

Therefore, the image pickup module 10 has a high reliability for the bonding portions and a high yield percentage. In addition, since the bonding is performed by applying energy, the reliability of the bonding portions is higher than the bonding using a conductive resin and the like.

For example, in the case of thermal bonding, when a heating tool is heated to a temperature between 100 to 400 degrees Celsius, the heating tool is pressed against the distal end portions of the flying leads 31. The flying leads 31 may be bonded one by one or a plurality of flying leads 31 may be bonded simultaneously, depending on the specs of the heating tool. In any case, heat is locally applied only to the distal end portions of the flying leads 31, which prevents damage from occurring at the light-receiving portion 21 as a semiconductor circuit.

In addition, when the bonding surfaces of the flying lead 31 and the surfaces of the bumps 23 are made of gold (Au), ultrasonic bonding is also possible. In the ultrasound bonding, heating is hardly required, which prevents damage from occurring specifically at the light-receiving portion 21.

After the flying leads 31 are bonded, a sealing resin 35 as a sealing portion that covers and seals the flying leads 31 is disposed. The sealing resin 35 contributes to the protection of the flying leads 31 made of metal conducting body and improvement of the connection strength between the image pickup chip 20 and the wiring board 30.

A thermo-curing epoxy resin, for example, is used as the sealing resin 35. That is, a liquid resin in the uncured state is disposed so as to cover the flying leads 31 using a dispensing method, for example, and thereafter thermo-curing treatment is performed at the temperature between 80 to 120 degrees Celsius, for example. The curing temperature is set to a temperature equal to or higher than the temperature required for the resin to be sufficiently cured and lower than the temperature at which damage occurs at the light-receiving portion 21.

Since the thermo-curing temperature of the sealing resin 35 is low, there is no possibility that damage occurs at the light-receiving portion 21. Note that the curing method may be selected from any one of the thermo-curing method, the UV curing method, the combination of the UV curing method and the thermo-curing method, the combination of the UV curing method and a moisture curing method, a room temperature curing method, or the like, depending on the type of resin, as long as a desired property is satisfied.

The image pickup module 10 for endoscope is inserted into a disposing hole of a distal end member of the endoscope and fixed with adhesive. The space between the image pickup module 10 and the disposing hole is sealed with a sealing resin. The adhesive and the sealing resin preferably include a filler with high heat conductivity. For example, silica, metal powder, alumina, aluminum nitride or the like is used as the filler, and silicone resin, acrylic resin, or the like is used as the sealing resin.

The endoscope 1, which includes the image pickup module 10 having high reliability for the bonding portion between the image pickup chip 20 and the wiring board 30, has high reliability.

Second Embodiment

Next, description will be made on an image pickup module 10A according to the second embodiment. The image pickup module 10A is similar to the image pickup module 10. Therefore, the same constituent elements are attached with the same reference numerals and description thereof will be omitted.

Figure 4:
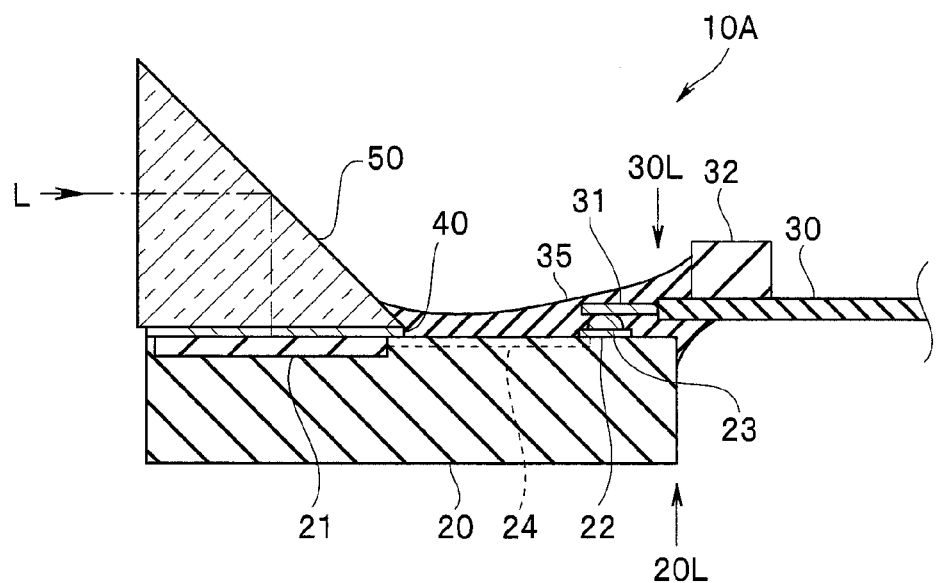
FIG. 4 is a cross-sectional view showing a configuration of an image pickup module according to a second embodiment.

As shown in FIG. 4, an electronic component 32 is surface-mounted on a wiring board 30 of the image pickup module 10A. A sealing resin 35 is formed by performing curing treatment on a liquid resin disposed between the prism 50 and the electronic component 32.

The electronic component 32 is disposed near the light-receiving portion 21 for primary treatment of an image pickup signal from the light-receiving portion 21, for example.

When the viscosity of the liquid resin is high, a hollow portion is likely to be created on the lower surface sides of the flying leads 31. On the other hand, when the viscosity of the liquid resin is low, the liquid resin is likely to flow out, and the thickness of the sealing resin 35 on the upper portions of the flying leads is likely to be reduced.

Therefore, when the shape of the electronic component 32 in a planar view is substantially rectangular, it is preferable to arrange the electronic component 32 such that the major axis direction of the electronic component 32 is parallel to the end surface 30L of the wiring board 30. The side surface of the electronic component 32 becomes a wall, thereby preventing the liquid resin from flowing out. That is, the liquid resin remains between the prism 50 and the electronic component 32. As a result, it is easy to form the sealing resin 35 with sufficient thickness also on the upper portions of the flying leads 31. That is, arranging the electronic component 32 at a predetermined position enables an additional function other than signal processing to be applied to the electronic component 32.

A chip type capacitor, for example, can be preferably used as the electronic component 32. It is preferable for the electronic component 32 to have a width (major axis dimension) substantially equal to the width of the sealing resin 35 (arrangement width of the plurality of electrodes 22). When an electronic component having a small width is used, a plurality of electronic components are continuously disposed, to thereby be capable of preventing the liquid resin from flowing out.

The image pickup module 10A has the same effects as those of the image pickup module 10. In addition, the image pickup module 10A is capable of surely sealing the flying leads 31 with the sealing resin 35, which provides high reliability for the bonding portions.

Third Embodiment

Next, description will be made on an image pickup module 10B according to the third embodiment. The image pickup module 10B is similar to the image pickup module 10 and the like. Therefore, the same constituent elements are attached with the same reference numerals and description thereof will be omitted.

Figure 5:
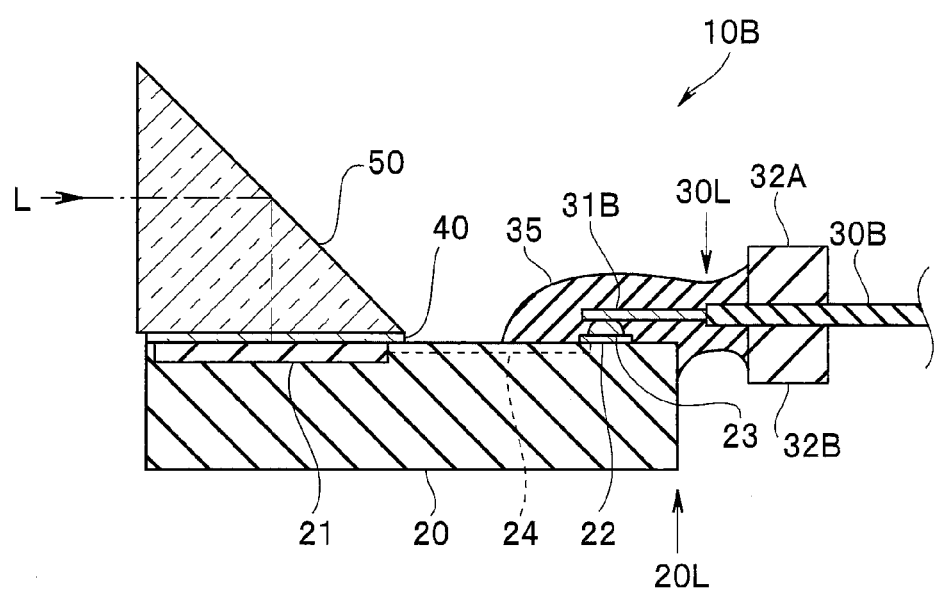
FIG. 5 is a cross-sectional view showing a configuration of an image pickup module according to a third embodiment.

As shown in FIG. 5, the image pickup module 10B is configured such that an end surface 20L of the image pickup chip 20 and an end surface 30L of the wiring board 30 do not overlap each other. With the image pickup module 10B, when a liquid resin is applied, the liquid resin is spread also to the rear surface sides of the flying leads 31 from the gap between the end surface 20L and the end surface 30L which do not overlap each other. Such a configuration is not likely to create a hollow portion on the rear surface sides of the flying leads 31.

The image pickup module 1 OB has the same effects as those of the image pickup module 10 and the like. In addition, it is easy for the image pickup module 10B to seal the flying leads more surely with the sealing resin 35. Furthermore, the strength of the flying leads 31 can be increased with the sealing resin 35.

Fourth Embodiment

Next, description will be made on an image pickup module 10C according to the fourth embodiment. The image pickup module 10C is similar to the image pickup module 10 and the like. Therefore, the same constituent elements are attached with the same reference numerals and description thereof will be omitted.

Figure 6:
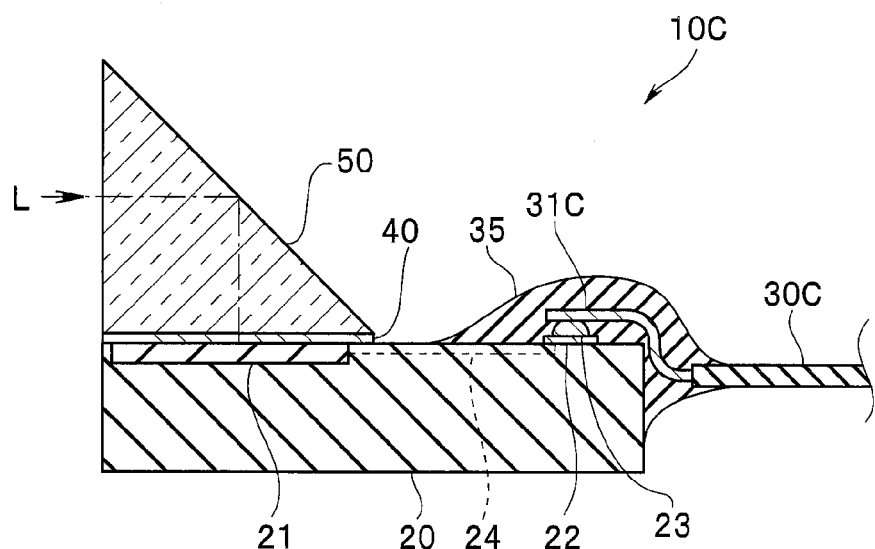
FIG. 6 is a cross-sectional view showing a configuration of an image pickup module according to a fourth embodiment.

As shown in FIG. 6, the image pickup module 10C is configured such that an end surface 20L of an image pickup chip 20 and an end surface 30L of the wiring board 30 do not overlap each other, and flying leads 31 are bent.

The image pickup module 10C has the same effects as those of the image pickup module 10 and the like. Furthermore, the image pickup module 10C not only has high bonding strength but also has high degree of freedom of design. Therefore, the image pickup module 10C can be configured in various ways.

Fifth Embodiment

Next, description will be made on an image pickup module 10D according to the fifth embodiment. The image pickup module 10D is similar to the image pickup module 10 and the like. Therefore, the same constituent elements are attached with the same reference numerals and description thereof will be omitted.

Figure 7:
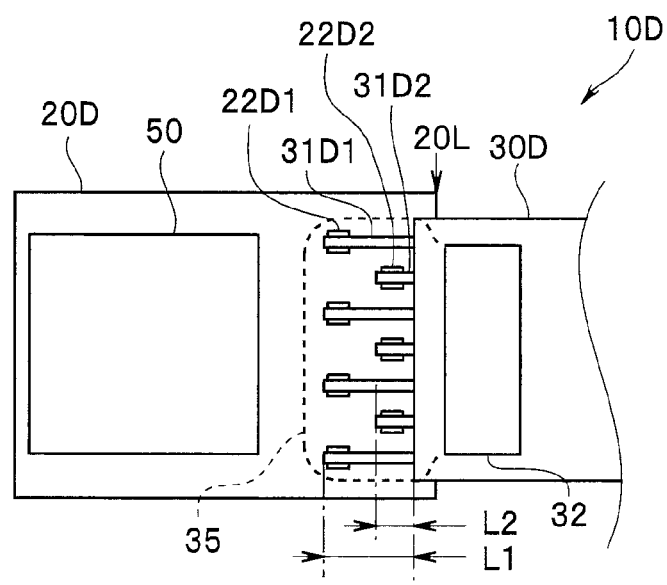
FIG. 7 is a plan view showing an upper surface of an image pickup module according to a fifth embodiment.

As shown in FIG. 7, the image pickup module 10D is configured such that the electrodes 22D1 and 22D2 whose distances from the end surface 20L are different are formed on the main surface, and a wiring board 30D includes flying leads 31D1, 31D2 which have different lengths.

That is, the flying lead 31D1 having a length L1 is connected with the electrode 22D1 whose distance from the end surface 20L is longer, and the flying lead 31D2 having a length L2 is connected with the electrode 22D2 whose distance from the end surface 20L is shorter. The electrodes 22D1, 22D2 and the flying leads 31D1, 31D2 are arranged alternately.

The image pickup module 10D has the same effects as those of the image pickup module 10 and the like. Furthermore, the space between the bonding portions is large, which enables easy manufacturing.

The present invention is not limited to the above-described embodiments and various changes and modifications are possible in a range without changing the gist of the present invention.

What is claimed is:

1. An image pickup module comprising:
   an image pickup chip including a main surface on which a light-receiving portion of an image pickup device and a plurality of electrodes connected to the light-receiving portion are formed;
   a wiring board including flying leads bonded to the respective plurality of electrodes; and
   a sealing portion that seals the flying leads;
   wherein an electronic component is surface-mounted on the wiring board,
   the sealing portion is formed by curing a liquid resin disposed between the optical component and the electronic component; and
   the sealing portion is in contact with the electronic component.

2. The image pickup module according to claim 1, wherein the flying leads are bonded to the electrodes by locally applying energy to distal end portions of the flying leads from an upper side of the distal end portions.

3. The image pickup module according to claim 1, further comprising an optical component that changes a direction of incident light from a direction parallel to the main surface such that the incident light is incident on the light-receiving portion.

4. The image pickup module according to claim 1, wherein an end surface of the image pickup chip and an end surface of the wiring board do not overlap each other, and
   both surfaces of a distal end portion of the wiring board are sealed by the sealing portion formed by curing a liquid resin.

5. The image pickup module according to claim 4, wherein the flying leads are bent.

6. The image pickup module according to claim 3, wherein the image pickup chip includes, on the main surface thereof, electrodes whose distances from the end surface of the image pickup chip are different, and the wiring board includes flying leads having different lengths.

7. The image pickup module according to claim 3, wherein the sealing portion is also in contact with the optical component.

* * * * *